United States Patent [19]

Lindquist

[11] 4,207,287
[45] Jun. 10, 1980

[54] CONTACT LENS STERILIZER APPARATUS

[75] Inventor: Robert H. Lindquist, Berkeley, Calif.

[73] Assignee: Chevron Research Company, San Francisco, Calif.

[21] Appl. No.: 29,098

[22] Filed: Apr. 11, 1979

Related U.S. Application Data

[63] Continuation of Ser. No. 819,314, Jul. 27, 1977, abandoned.

[51] Int. Cl.$^2$ .............................................. A61L 3/00
[52] U.S. Cl. ........................................... 422/33; 141/1; 141/91
[58] Field of Search .................................. 422/33–37, 422/28, 295, 296, 297; 141/1, 2, 3, 18, 20, 91, 327, 346–349

[56] References Cited

U.S. PATENT DOCUMENTS

| | | | |
|---|---|---|---|
| 2,899,266 | 8/1959 | Gewalt et al. | 422/30 |
| 2,965,936 | 12/1960 | Kaye | 422/34 X |
| 3,342,544 | 9/1967 | Curiel | 422/300 |
| 3,473,886 | 10/1969 | Leeds | 422/295 |
| 3,476,507 | 11/1969 | Leeds | 422/35 |
| 3,645,284 | 2/1972 | Krezanoski et al. | 206/5.1 |
| 3,856,571 | 12/1974 | Sherman | 206/5.1 X |
| 3,900,288 | 8/1975 | Levine | 422/33 |

Primary Examiner—Arnold Turk
Attorney, Agent, or Firm—R. L. Freeland, Jr.; J. A. Buchanan, Jr.

[57] ABSTRACT

Method for sterilizing soft contact lenses and the like using methoxymethane while the lenses are in a liquid-wetted state. Methoxymethane on the water-wet surface for a sufficient time kills the microorganisms (bacteria, molds and yeasts) that invade and are entrapped in the pores and irregular surfaces of the hydrophilic materials from which such soft contact lenses are made. An easily portable apparatus for applying this sterilization technique to the lenses is also disclosed. It includes a lens holder that can be held in a chamber that can be pressure-isolated to receive the methoxymethane gas from portable sources. In one form, an indicator shows that the lenses are under sterilization pressure. This novel arrangement dispenses with the inconvenience of using prolonged steaming, or questionable sterilization in disinfecting fluids which may affect the composition of the soft contact lens.

4 Claims, 5 Drawing Figures

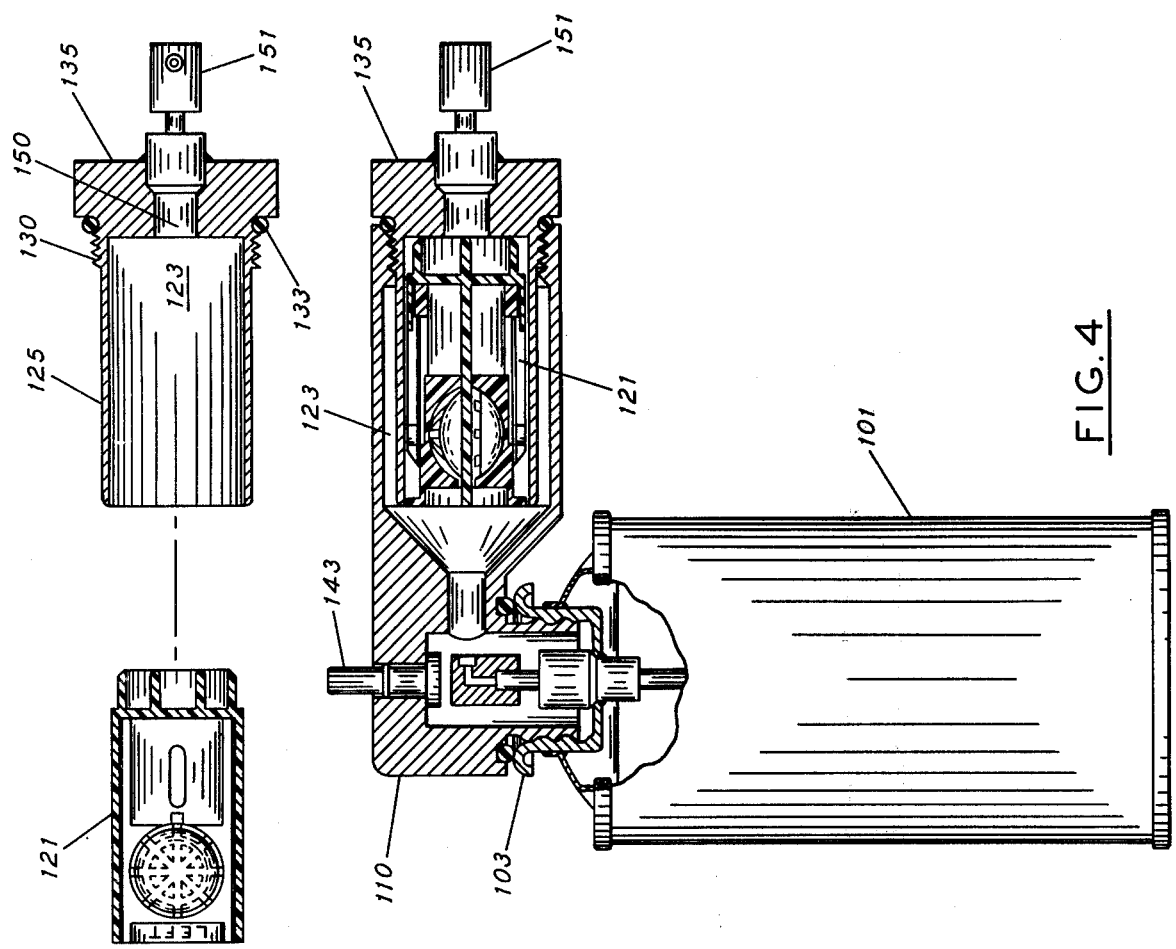
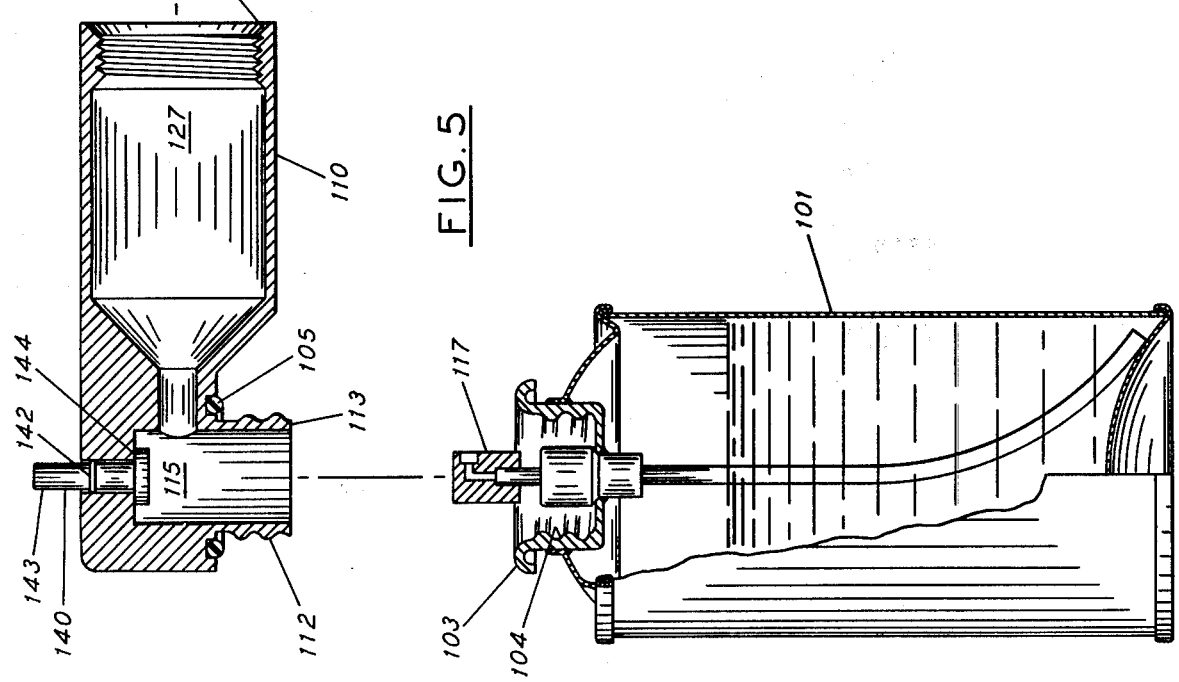

CONTACT LENS STERILIZER APPARATUS

This is a continuation of application Ser. No. 819,314, filed July 27, 1977, and now abandoned.

FIELD OF THE INVENTION

The present invention relates to a method of, and apparatus for, sterilizing contact lenses and the like. More particularly, it relates to sterilization of so-called soft contact lenses by the use of methoxymethane in liquid-gaseous form.

It is a particular object of the present invention to provide a method of sterilizing soft contact lenses, such as those made of poly 2-hydroxyethyl methacrylate or polyvinyl pyrrolidone, which must be kept water-moist at all times, both during wear and sterilization. In carrying out the object of the invention, means are provided for first washing the contact lens in a suitable holder and then exposing the lens while in the holder to sterilization by methoxymethane in a pressurizable chamber. The chamber can be isolated from the atmosphere to permit injection of the sterilizing gas so that it will contact the wetted lenses to kill bacteria, molds, and yeasts such as coliform, pseudomonas or other foreign organisms, that can grow in and on the porous surface of the lens material. Such an arrangement makes possible sterilization of the contact lens material without damage to the material and without the need to use saline solutions and steam generators for exposing the lenses to sterilizing steam over a prolonged period of time. Likewise, it obviates the need to soak the lenses in a solution containing bactericides, which may leave a harmful residue on the lens surface or be absorbed into the contact lens material, from whence it can dissolve in a wearer's eye fluid.

BACKGROUND OF THE INVENTION

Soft contact lenses, ordinarly made of poly 2-hydroxyethyl methacrylate, polyvinyl pyrrolidone, or the like, have become quite popular with eyeglass wearers, and particularly those who need optical correction for nearsightedness. While in part such wear is cosmetic in nature, they are conceded to be more comfortable for prolonged wear than "hard" contact lenses. Additionally, the material from which soft contact lenses are formed is virtually unbreakable and minimize the hazard of damage to the wearer's eyes, as compared to hard contact lenses. Unfortunately, these materials are porous and readily absorb liquids. In fact, this type of material depends for its softness upon the fact that it does absorb liquid, including the natural tear fluid of the eyes. Because of this porous characteristic, they also readily absorb bacteria, molds and yeasts in normal wear, and require sterilization on a regular basis. Recommended sterilization is at least daily, if the wearer is to avoid possible eye infections. In the cleaning process, it is necessary that the lenses be removed and placed in a sterilizing solution or steamed, according to the prior art, for a period of time sufficient to assure kill of the microorganisms. Unfortunately, in removal and sterilizing, the contact lenses normally develop scratches and abraded spots in the lens surface due to fingernails and other rough surfaces. Such imperfections in the surfaces add to the possibility of microorganism growth in the material.

It is, of course, essential that the material not dry out, because, if dry, it tends to change dimensions and crack. Accordingly, the contact lenses must be sterilized while wet, or at least moist. It has been proposed heretofore to sterilize such articles with ethylene oxide in a gaseous state. (See for example in U.S. Pat. No. 3,473,886, Leeds, or U.S. Pat. No. 2,965,936, Kaye.) However, ethylene oxide gas is not particularly effective in sterilizing water-wet materials and additionally, because ethylene oxide is a reactive gas, it may interact with the material to cause deterioration. As mentioned before, the use of sterilizing liquids, such as hydrogen peroxide solutions (recommended for polyvinyl pyrrolidone-containing lenses) is undesirable because such sterilization requires a prolonged period of time (several hours). Further, if hydrogen peroxide is retained in the porous surface of the soft contact lens, it has a tendency to dehydrate the eyes and may cause irritation. In addition, unless the concentration of the solution is high, it is not fully effective as a sterilizing agent.

The most popular system for cleaning soft contact lenses at the present time is to steam the lenses for, say, 15 to 20 minutes after they have been thoroughly washed in a saline solution, freshly made, using distilled water. Sterilizing is normally carried out in a steam generator by evaporating distilled water. The difficulty of obtaining a suitable source of heat, such as electrical power, and the necessity for carrying a supply of distilled water and salt, renders the method effective only under the most stable living conditions for the user. In particular, in traveling or moving about, the user frequently finds such apparatus and materials quite inconvenient for regular daily use.

SUMMARY OF THE INVENTION

In accordance with the present invention, a readily portable system for sterilizing soft contact lenses is provided wherein the individual lenses may be water-wetted or moistened with ordinary water in an article-receiving chamber which may include a holder for the individual lenses, such as those normally used for distinguishing "right" and "left" lenses and holding the two lenses in a simple carrier. The chamber is arranged to disconnectably receive said holder so that the lenses inside the holder are exposable, in their water-wetted condition, to a sterilizing gas admitted to the chamber, after it is isolated from the atmosphere. The sterilizing gas, preferably methoxymethane in gaseous form, is then introduced into the chamber to contact the moist lenses within the article holder. Further in accordance with the invention, the chamber may be provided with a sterilizing gas pressure indicator so that the user can be assured that the lenses are being held at above atmospheric pressure for the required sterilization period of several minutes, say 15. In this way, the methoxymethane may adequately interact with microorganisms present on and in the porous surfaces, including any scratches or grinding marks on the surfaces of the lenses. Means are provided to release gas from the chamber after the chamber has been isolated from the pressure source, so that gas is not lost excessively from the source. The chamber may then be opened for removal of the holder and lenses.

A particular aspect of the sterilization process of the present invention, when so carried out, is that a slight cloudiness of the lenses may result. This indicates that a slight amount of the methoxymethane is still present in the porous material. However, after a very short period, the material again clears, indicating visually that all methoxymethane has evaporated under atmospheric conditions, so that the lenses are sterile and safe for insertion over the wearer's eye. Such visual evidence is particularly useful to indicate both sterility and the absence of any possible irritating material in the contact lens itself.

Further in accordance with the present invention, the holder and the chamber are so arranged that with the contact lenses in the holder and within the chamber, the entire chamber may be submerged in water for initial cleaning. Any excess water may then be drained prior to connection of the chamber to a source of methoxymethane sterilizing gas through the pressure isolation means.

Further objects and advantages of the present invention will become apparent from the following detailed description taken into conjunction with the accompanying drawings which form a part of the present specification.

BRIEF DESCRIPTION OF THE DRAWINGS

In the drawings,

FIG. 4 is a side elevation, partially in cross-section, of an alternate embodiment of the invention in its assembled form; and FIG. 5 is an exploded view of the assembled arrangement of FIG. 4.

DETAILED DESCRIPTION OF THE INVENTION

Figure 1:
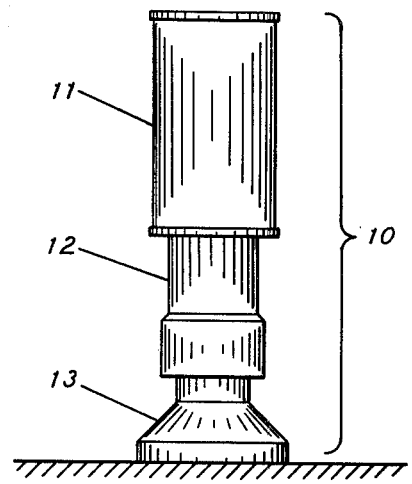
FIG. 1 is a side elevation view of an article-sterilizing apparatus, constructed in accordance with the present invention, in its assembled form.

Referring now to the drawings, and in particular to FIG. 1, there is shown a hand-holdable lens sterilizing assembly generally designated as 10. The unit generally comprises a source of sterilizing gas 11, preferably condensed to liquid form, indicated as being contained in a small, pressure can, say one holding 6 to 8 fluid ounces, a pressure chamber section 12; and a stand member 13, which also functions as a handle for screwing the sections of pressure chamber 13 into a vapor-sealing relationship with the source or container 11.

Figure 3:
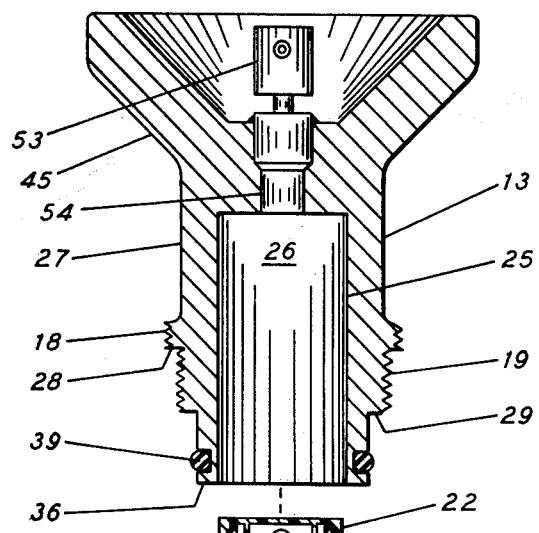
FIG. 3 is a view similar to FIG. 2, with the chamber and holder disassembled from the valving mechanism and the source of sterilizing gas.
Figure 3:
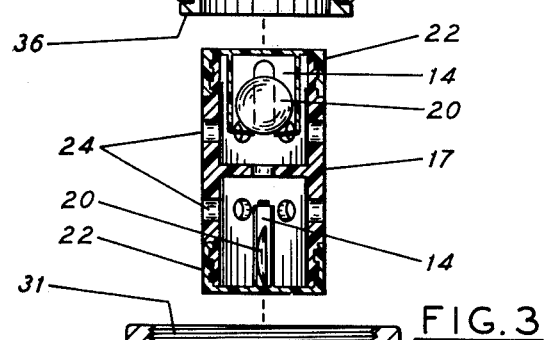

As best seen in FIG. 3, a lens holder 17 is adapted to hold a pair of contact lenses 20 in receivers formed in opposite ends of holder 17. As is well understood, these opposite ends are usually marked with indications as to right and left lenses. In the present embodiment, each lens 20 is held in a pocket 14 formed with screwable cap 22 arranged to engage the threads on the opposite ends of the body of holder 17. As indicated by the holes 24 in body 17, the lenses may be flushed with water by immersing holder 17 containing the lenses in any suitable solution. Normally, this is distilled water, but in accordance with the present invention may be any suitable cleaning fluid such as ordinary water.

Holder 17 is adapted to be received within chamber 26 formed by bore 25 in stand or base 13. To isolate chamber 26 from atmosphere, elongated cylindrical portion 27 of base 13 includes two sets of threads 18 and 19. Threads 18 are formed on shoulder 28 and a second set of threads 19 are on reduced section 29. Preferably threads 18 are formed with a right-hand thread so that they will first engage complementary right-hand threads 31 on chamber section or means 12. After threads 18 on shoulder 28 have been completely screwed through threads 31, the relieved portion 47 of bore 34 permits threads 19 to be screwed into threads 33. The purpose of such an arrangement is to prevent the entire assembly 13 from accidently being expelled from bore 34 in chamber means 12 under gas pressure applied from source 11, as will be explained hereinbelow. Threads 19 on reduced shoulder 29 are then arranged to engage complementary threads 33, both indicated as being left-handed, after the forward end 36 of base 13 is inserted deeply enough into inner bore 37, so that O-ring 39 is seated against the smooth surface of bore 37. The fit between O-ring 39 and bore 37 then assures that the chamber is closed from atmospheric pressure prior to activation of the valving means 40 to admit the liquefied gas from source 11. Valve means 40 comprises valve stem 41, spring 42 and valve head 43 whose seat is formed by O-ring 44 at the transition in the passageway 50 from source 11 to bore 37 in chamber means 12.

As noted, threads 33 and 19 are preferably left-handed, so that securing of the chamber means against atmospheric pressure is by rotating handle 45 counter-clockwise relative to chamber means 12 and source 11 until threads 19 seat by shoulder 29 landing on the shoulder 49 at the end of bore 37. In this position, end 36 of chamber means 13 contacts the upper end of valve stem 41 to compress spring 42 into the position shown in FIG. 2. In chamber means 12 valve head 43 and O-ring 44 are thus unseated to permit sterilizing gas from source 11 to enter the sealed chamber formed by chambers 34 and 26 through radial passageways 51 in valve stem 41.

Figure 2:
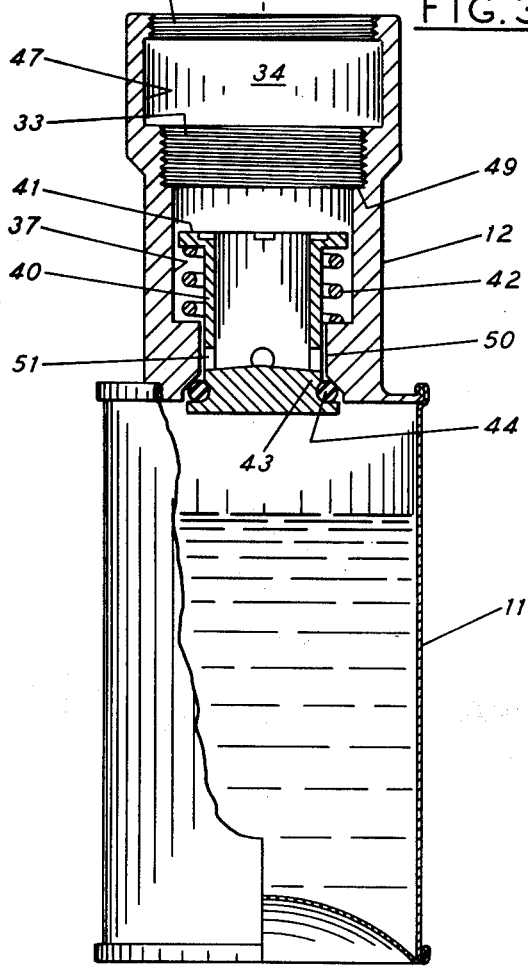
FIG. 2 is an enlarged vertical elevation view similar to FIG. 1, with the assembly inverted and partially in section to show the valving arrangement for exposing the contact lenses and their holder to the sterilizing gas.
Figure 2:
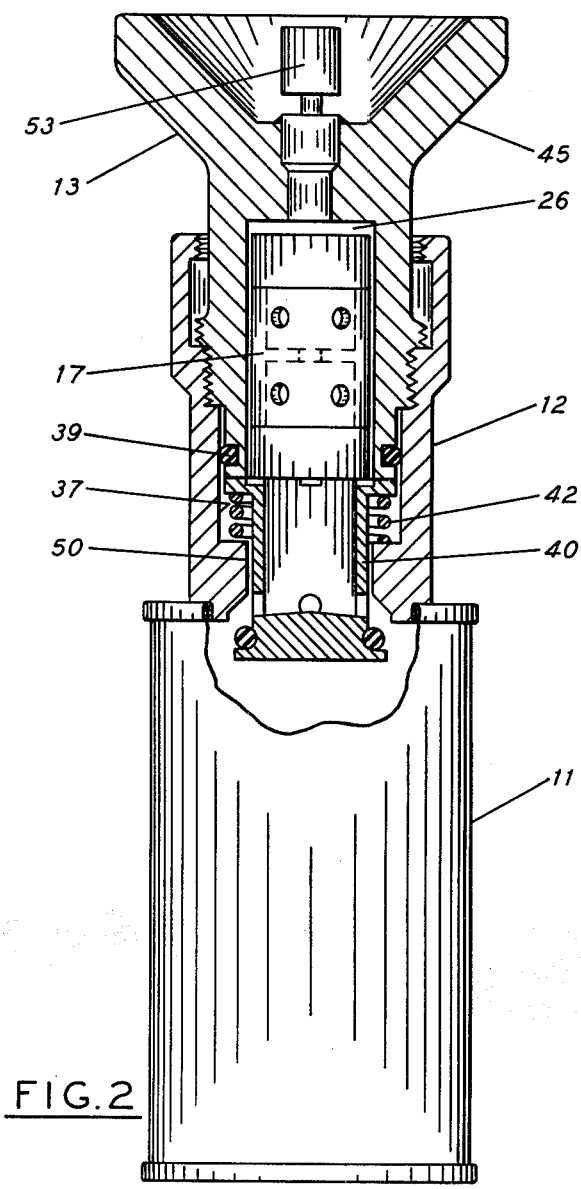

Preferably, the assembly, as shown in FIG. 2 is then inverted so that the lenses are fully immersed in the sterilizing fluid by turning it into the position shown in FIG. 1, for a period of time, say 15 minutes. In this position, the lenses are in full liquid contact with the methoxymethane rather than merely exposed to the gaseous phase of the liquid. Such liquid contact of the lenses is possible because of the hydrophilic nature of methoxymethane with the water wet lenses. At the end of the required sterilization period, the assembly is again inverted to the position as shown in FIG. 2. This permits the liquefied gas to drain from chamber 26 and holder 17. Valve means 40 is then closed by reverse-screwing handle 45 to permit spring 42 to close valve head 43 to seat O-ring 44 against the seat of chamber means 12. Only a limited amount of residual gas and some small amount of liquid will then remain in pressure sterilizing chamber 12. Thus, after closure of valve 40, the pressure in the chamber 12 may be relieved as by spray valve assembly 53, which is connected to bore 54 to relieve gaseous pressure through the upper end of the chamber 26. No detail is shown of this valve structure, since it is a typical aerosol valve, in general use on conventional spray-can assemblies.

FIGS. 4 and 5 illustrate an alternative embodiment for carrying out the method of the present invention. As particularly distinguished from the arrangement of FIGS. 1-3, the system is adapted to be used with a modified aerosol spray can of the type used for dispensing household detergent, shaving cream, and the like. However, as distinguished from such conventional spray cans, the upper end of spray can 101 terminates in a cup 103 having internal threads 104 adapted to receive the threaded portion 113 of pressure chamber assembly 110. Threads 112 and o-ring 105 on the outside of extension 113 secure together assembly 110 and can 101. This relationship is best seen in FIG. 4. In the particular arrangement shown here, the soft contact lenses are adapted to be sterilized entirely by gaseous methoxymethane, since in this embodiment a typical one-way aerosol valve assembly, such as 117, operates only to release fluid from the source, spray can or container 101, and does not purposefully permit back flow from chamber 127 of assembly 110 into can 101.

However, as with the previous embodiment, holder 121 includes two receptacles for soft contact lenses at its opposite ends. Holder 121 is adapted to be received in bore 123 of tube 125 and in turn, tube 125 is adapted to be received by bore or chamber 127 of chamber means 110. Tube 125 is secured to chamber means 110 by threads 130 and sealed by O-ring 133 seating between the shoulder on end head 135 on tube 125 and the beveled end 136 of chamber means 110. As further distinguised from the arrangement of FIGS. 1-3, an actuating mechanism such as plunger 140 may depress aerosol valve 117 to admit gaseous sterilizing fluid into chamber 127 and holder 121 after assembly to isolate the chamber from atmospheric pressure as seen in FIG. 4. A particular feature of the valve actuating mechanism 140 is that O-ring 142 is seated in a groove on stem 143 of actuator 140. It will be particularly noted that this arrangement is not spring-loaded. Accordingly, when gas under pressure is admitted into chamber 110 and into the bore 115 in extension 113, a pressure higher than atmospheric across O-ring 142 forces valve head 144 against the inner end of bore 115. This indicates that the sterilizing chamber is under pressure. After the lenses have been suitably sterilized for the prescribed period of time, the holder may be removed by first depressing aerosol valve 151 in bore 150 through head 135 to relieve the pressure in tube 123.

From the foregoing description and detailed embodiment of the present invention, it will be seen that there has been provided a simplified system for adequately and thoroughly sterilizing soft contact lenses. Of course, it will be understood that any other small articles requiring microorganism decontamination may be similarly treated in this arrangement and by using the same method.

In summary, the articles to be sterilized are at first supported in an article holder so that they can be water-wet and then disposed in a pressure-isolating chamber so that methoxymethane may be admitted under pressure to contact the wetted articles, either as a gas or as a liquefied gas. After such contacting, the pressure is reduced in the chamber so that the article holder and the lenses may be removed.

While only a few embodiments have been described, it will be apparent that further changes or modifications can be made in the equipment, or in the method, without departing from the spirit and scope of the present invention. All such changes or modifications falling within the scope of the appended claims are intended to be included.

What is claimed is:

1. Apparatus for sterilizing an article comprising:
   means forming an article-receiving chamber;
   an article holder having liquid passageways formed therein to permit liquid and gas contact of an article therein after enclosure in said holder;
   first threaded closure means for enclosing said article holder in said chamber means;
   additional threaded means for threadably securing said chamber means to a source of sterilizing fluid;
   a source of sterilizing fluid; fluid passage means formed between said source and said chamber means through said additional threaded securing means;
   sealing means between said chamber means and said fluid passage means operable in response to engagement of said additional threaded means for isolating said chamber means from the atmosphere and sealing said chamber to said source of sterilizing fluid;
   valve means in said fluid passage means, said valve means being operable after actuation of said sealing means so that upon actuation of said valve means an article in said chamber means may be exposed to sterilizing fluid from said source;
   said valve means being further operable to close said passage means to isolate said chamber means from said source while maintaining said chamber means isolated from the atmosphere after exposure of said article and before disassembly of said chamber means from said source;
   second fluid passage means formed in said chamber means and relief valve means for controlling flow through said second fluid passage means for reducing the pressure in said chamber means substantially to atmospheric pressure before disengagement of said additional threaded means and said sealing means.

2. Hand-holdable apparatus for sterilizing contact lenses comprising:
   a holder for detachably holding contact lenses to be sterilized;
   said holder including fluid flow passageways formed therein to permit lenses being held thereby selectively to be wetted with an aqueous solution or contacted by a sterilizing fluid;
   means forming a chamber having one end closed and the other end thereof open to receive said holder concentrically therein;
   a tubular member for concentrically receiving at least a portion of the open end of said chamber means;
   threaded closure means formed exterior of said chamber means, and interior of said concentric tubular member for enclosing said holder within said chamber means;
   a source of sterilizing fluid at superatmospheric pressure;
   said tubular member being attached to said source of sterilizing fluid forming a fluid passageway;
   said chamber means and said tubular member including additional complementary mating thread means for connecting said chamber means to said tubular means to permit the lenses being held by said holder to be exposed to the sterilizing fluid at superatmospheric pressure within said chamber;
   sealing means between said chamber means and said tubular member to seal said chamber and said source in a gas-tight relationship when the additional complementary mating thread means are engaged;
   first valve means in said fluid passageway;
   valve operating means operable by displacement of said tubular member for controllably injecting through said first valve means said sterilizing fluid under superatmospheric pressure from said source into said chamber;

a pressure relief passageway formed between said closed end of said chamber and atmosphere;

second valve means in said relief passageway operable exteriorly of said chamber for reducing the pressure in said chamber to atmospheric pressure after closure of said first valve means to isolate said chamber from said source, to permit removal of said holder and the sterilized lenses from said chamber.

3. Hand-holdable apparatus for sterilizing an article comprising:

a holder for an article;

said holder including fluid flow means formed therein to permit wetting of said article with an aqueous solution while said article is in said holder; p1 pressure chamber means arranged to disconnectably receive said holder therein so that said article may be exposed to the atmosphere within said chamber;

first threaded closure means for enclosing said holder in said chamber means;

additional threaded closure means for sealing a source of sterilizing fluid to said chamber means;

a source of sterilizing fluid;

sealing means between said chamber and said source operable by engagement of said additional threaded closure means for isolating said chamber means from the atmosphere and sealing said chamber means to said source of sterilizing fluid;

fluid passage means formed through said sealing means and said additional threaded closure means;

first valve means in said passage means;

valve-actuating means operable after actuation of said sealing means to control injection of a predetermined quantity of sterilizing fluid from said source at above atmospheric pressure into said chamber means through said fluid passage means while the wetted article is exposed within said chamber means thereby to contact the wetted article with said sterilizing fluid; and relief valve means secured to said chamber means for reducing the pressure in said chamber to substantially atmospheric conditions so that said holder may be withdrawn from said chamber to permit removal of the sterilized article from said holder.

4. Apparatus in accordance with claim 3 wherein said article holder includes means for support of a contact lens.

* * * * *